United States Patent [19]

Daniels

[11] Patent Number: 4,708,718

[45] Date of Patent: Nov. 24, 1987

[54] HYPERTHERMIC TREATMENT OF TUMORS

[75] Inventor: John R. Daniels, Pacific Palisades, Calif.

[73] Assignee: Target Therapeutics, Los Angeles, Calif.

[21] Appl. No.: 751,605

[22] Filed: Jul. 2, 1985

[51] Int. Cl.$^4$ ............................................. A61M 31/00
[52] U.S. Cl. ....................................... 604/53; 604/20; 604/41; 128/1 R; 128/DIG. 8; 424/499; 530/356
[58] Field of Search ...................... 604/20, 52, 53, 101, 604/41, 97, 98, 368; 128/1.1, DIG. 8, 324 R, 1 R; 260/123.7; 424/14; 530/356

[56] References Cited

U.S. PATENT DOCUMENTS

| | | | |
|---|---|---|---|
| 4,106,488 | 8/1978 | Gordon | 128/1.1 |
| 4,303,636 | 12/1981 | Gordon | 128/1.1 |
| 4,323,056 | 4/1982 | Borrelli et al. | 604/52 |
| 4,345,588 | 8/1982 | Widder et al. | 604/52 |
| 4,444,971 | 9/1983 | LeVeen et al. | 604/53 |
| 4,558,690 | 12/1985 | Joyce | 604/20 |
| 4,569,836 | 2/1986 | Gordon | 128/1.1 |

*Primary Examiner*—C. Fred Rosenbaum
*Assistant Examiner*—John D. Ferros
*Attorney, Agent, or Firm*—Ciotti, Murashige, Irella & Manella

[57] ABSTRACT

A method of treating a solid tumor, including the steps of localizing the tumor and the arterial vessel that supplies it, and injecting into the vessel, a vaso-occlusive collagen material adapted to produce occlusion of vessels having lumen diameters between about 10 and 150 microns. The injected material is effective to produce occlusion of the secondary and tertiary vessels supplying the tumor, distal to the collateral blood vessels which may also supply the tumor. The region of the occluded tumor is heated under conditions that produce tissue necrosis selectively in the occluded tumor tissue.

15 Claims, 1 Drawing Figure

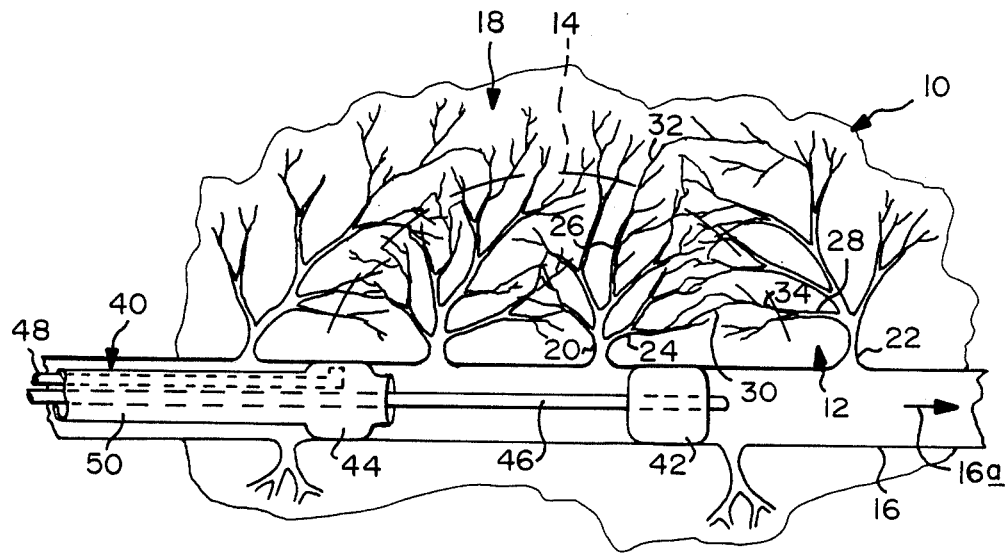

HYPERTHERMIC TREATMENT OF TUMORS

1. FIELD OF THE INVENTION

The present invention relates to hyperthermic treatment of solid tumors and, more particularly, to a method for selective hyperthermic enhancement by small-vessel vaso-occlusion.

2. REFERENCES

1. Meyer, J. L., et al, *Cancer Res* (Suppl.), 44:4745s (1984).
2. Hahn, G. M., *Cancer Res* (Suppl.), 44:4906s (1984).
3. Stewart, J. R., *Cancer Res* (Suppl.), 44:4902s (1984).
4. Baker, H. W., et al, *Am J Surg,* 143:586 (1982).
5. Hahn, E. W., et al, *Cancer Res,* 34:3117 (1974).
6. Kase, K., *Nature,* 255:228 (1975).
7. Shibata, H. R., et al, *Prog Clin Cancer,* 2:33 (1966).
8. Kowal, D., et al, *Cancer Res,* 39:2285 (1979).
9. Rofstad, E. K., et al, *Int J Radiation Oncology Biol Phys,* 7:1685 (1981).
10. Le Veen, H. H., et al, *Am Surg,* 50:61 (1984).
11. Stewart, J. R., *Int J Radiation Oncology Biol Phys,* 9:197 (1982).
12. Dewhirst, M. W., et al, *Cancer Res* (Suppl.), 44:4772s (1984).

3. BACKGROUND OF THE INVENTION

Hyperthermia has been widely investigated for use in tumor therapy, either as a sole treatment modality or as an adjunct to radiation or chemotherapy (references 1–4). Hyperthermia offers a number of potential advantages for cancer treatment. Studies have shown that tumor cells are more susceptible to destruction by heat, due in part to the relatively greater hypoxia and lower pH in solid tumors (references 5, 6). The restricted blood flow in solid tumors, especially larger ones, reduces the ability of tumors to dissipate heat (reference 7). Hyperthermia has been shown to enhance the sensitivity of tumors to radiation and to chemotherapeutic agents (reference 1, 8). The side effects of hyperthermia on normal tissue are insignificant at temperatures less than 41.8° C., and hyperthermia can be used repeatedly without cumulative damage to normal tissue.

Despite its potential advantages, hyperthermic treatment of solid tumors has been found to provide rather limited selective tumor destruction heretofore. This limitation is due in part to the inability of hyperthermic treatment methods used in the prior art to produce a sufficient temperature differential between tumor and surrounding normal tissue, even though tumor tissue has a generally impaired ability to dissipate heat. Frequently at input energy levels which approach tolerance for normal tissues, there are areas within the tumor mass and along the more vascularized periphery which do not heat sufficiently (12).

Attempts to augment response to hyperthermic treatment by means of arterial clamping, have been reported (references 9–11). Occlusion of the regional artery supplying a tumor reduces the arterial pressure distal to the occlusion, which in theory has the potential for producing greater heat build-up in the clamped tumor tissue. In the studies reported, arterial clamping was, in fact, found to enhance the hyperthermic damage to tumor tissue. However, where heating patterns in clamped and unclamped tissue were examined, no differences were observed between tumor and adjacent normal tissues. The results suggest that the enhanced toxicity observed is related to metabolic effects of vaso-occlusion, rather than to differential heating. Therefore, arterial clamping, although beneficial, fails to provide a significant advantage in terms of temperature selectivity.

The desirability of creating a temperature differential in hyperthermic cancer treatment is related to the greater rate of tissue destruction which is known to occur at increasing tissue temperatures above about 42° C. The general rule is that each degree increase in tissue temperature approximately halves the time required to produce a given amount of tissue damage. Thus if a given amount of tissue damage results from heating the tissue at 42° C. for two hours, the same amount of damage is produced in an hour at 43° C., and in one-half hour at 44° C. Viewed another way, each one-degree increase in temperature differential can double the extent of selective tissue damage produced by heating the tissue for a given time.

4. SUMMARY OF THE INVENTION

It is therefore a general object of the invention to provide, for treating a tumor by hyperthermia, a method which is effective in producing a significant temperature differential between tumor and adjacent, non-tumor tissue.

Still another object of the invention is to provide such a method that can produce selective tumor toxicity through combined differential heating and long-term vaso-occlusion effects.

The method of the invention involves first, localizing a tumor of interest and the arterial vessel that supplies it. A collagen vaso-occlusive material adapted to produce occlusion of blood vessels having lumen diameters between about 10 and 150 microns is injected into the vessel, leading to vaso-occlusion of the secondary and tertiary vessels supplying the tumor, distal to the collateral blood vessels which may also supply the tumor. The tumor is then heated under conditions which produce tissue damage selectively in the occluded tumor tissue. The hyperthermia treatment may be combined with radiation or chemotherapy.

The vaso-occlusive material preferably includes a suspension of chemically cross-linked atelopeptide collagen which is adapted to persist in the occluded vessels, after injection, for a period of at least a week or more. The persistence of the material can be increased by increasing the degree of cross-linking of the collagen.

These and other objects and features of the invention will become more fully apparent from the following detailed description of the invention, when read in conjunction with the accompanying drawing.

BRIEF DESCRIPTION OF THE DRAWING

FIG. 1 is a simplified sectional view of a tissue region containing a solid tumor, illustrating the placement of a catheter used for injecting a vaso-occlusive material into the tissue, according to the method of the invention.

DETAILED DESCRIPTION OF THE INVENTION

The figure shows anatomical features of a tissue region 10 containing a solid tumor 12 which is to be treated according to the method of the invention. The upper portion of the tumor is defined by the dashed line seen at 14, and the lower portion, by an arterial vessel 16 which supplies the tumor with blood, in the direction of arrow 16a. The normal tissue surrounding the tumor is indicated generally at 18.

As shown in the figure, the tumor and surrounding tissue are supplied from a network of small blood vessels which branch from vessel 16. The network, which is shown in simplified form in the figure, includes (a) primary vessels, such as vessels 20, 22 branching from vessel 16; (b) secondary vessels, such as vessels 24, 26, 28 branching from the primary vessels; and (c) tertiary vessels, such as vessles 30, 32, 34 branching from the secondary vessels. The blood supply network also includes a capillary bed supplied by the smallest vessels. Vessel 16, which forms the trunk of the blood-supply network just described, has a typical lumen diameter between about 1 to 5 mm. The secondary and tertiary vessels characteristically have diameters ranging between about 10 to 500 microns, and the primary vessels, intermediate sizes, i.e., between about 200 and 1,000 microns.

It is observed from the figure that the secondary and tertiary vessels contain extensive interconnections, distal to their respective primary vessels. These interconnections form a collateral supply system which allows blood to be supplied to the smaller vessels from primary vessels other than those directly supplying blood from vessel 16. For example, tertiary vessel 30 within the tumor region may be supplied blood collaterally from primary vessel 22 disposed within normal tissue. Usually, the collateral system becomes an important supply source for the tissue only after primary vessels are blocked or otherwise damaged.

From the above description of a blood vessel network associated with a solid tumor, the limitations of arterial clamping, as a means of enhancing the effects of hyperthermia, can be appreciated more clearly. Assuming that vessel 16 is the smallest vessel in the network that can be clamped, and that the clamp is positioned upstream of the tumor region (to the left of the tumor in the figure), it is seen that the clamp would restrict blood flow nonselectively to the tumor and to the "downstream" normal tissue, as well. In addition, the collateral network on the upstream side of the clamp would partly compensate for the reduced blood flow to the tumor, particularly if the clamp were maintained in place over an extended period.

Having considered some general vascular features associated with a solid tumor, the steps used in treating a tumor according to the invention will now be described.

1. Localizing a Tumor Supply Vessel

The solid tumor, and the vessel(s) that supplies it are identified preferably by conventional angiographic procedures. In a typical method, a catheter designed to release a (radio-opaque) contrast material into the blood is threaded through the arterial system toward the suspected tumor site. The region of interest is monitored fluoroscopically as the contrast material is released. From the observed rates of flow of material through the vessels, and the patterns of accumulation of material in the tissue, the tumor(s) can be localized, and the major vessel(s) supplying the tumor identified. These methods are well understood by practitioners in the field.

2. Providing a Collagen Vaso-Occlusive Material

The invention uses, for vaso-occlusion, a collagen material adapted to produce occlusion of blood vessels having lumen diameters between about 10 and 150 microns. The material is preferably chemically cross-linked to produce a desired persistence in the occluded vessels after injection. As will be discussed, non-cross-linked material shows relatively poor persistence (less than a day), and material which is progressively more cross-linked shows progressively greater persistence, ranging from about one month for predominantly intrafibrillar cross-linking to more than three months for predominantly interfibrillar cross-linking.

The cross-linked collagen used in the invention is preferably prepared from an aqueous solution of atelopeptide collagen obtained as described in co-owned U.S. Pat. No. 4,140,537 and incorporated herein by reference. The collagen solution is reconstituted to form a suspension of collagen fibrils preferably by neutralizing the solution at a temperature between about 10° C. to 25° C. The ionic strength of the neutralized solution is preferably hypotonic relative to physiological conditions. Ionic strengths in the range of about 0.03 to about 0.1, preferably about 0.06, will typically be used. The neutralization involves raising the pH of the solution by adding an appropriate base or buffer, such as $Na_2HPO_4$ or $NaOH$, to a level at which the collagen in solution reaggregates into fibrils. Fibril formation occurs under these conditions at pHs in the range of about 4.9 and about 10.0. The final pH is preferably in the range of about 5 and 8. Within this range pHs below about 7 favor formation of fine, soft fibrils whereas pHs above about 7 favor formation of coarser fibrils, which may be more difficult to inject. The duration of the fiber formation step will normally be in the range of about $\frac{1}{2}$ to about 18 hr.

The injectability of the ultimate cross-linked material may be enhanced by forcing the suspension of collagen fibrils through a screen of defined pore size after or during the reconstitution step. This procedure, called "screening", provides a preferred starting material for the cross-linking step. Screening breaks up any aggregates that may be present in the reconstituted fibril suspension and gives a more uniform fibril size distribution. A preferred screening protocol is to repeatedly pass the fibril suspension through a 60 mesh stainless steel screen at about 5° C. and a flow rate of about 7–7.5 l/min about 2–3 hr after the fibers precipitate. The suspension is recirculated through the screen for about 4–5 hr, with about 35 passes through the screen being optimum. After the screening, the fiber suspension is incubated in the reconstitution medium for about 6 to 15 hr. The screening procedure is detailed in commonly owned U.S. patent application for Mechanically Sheared Collagen Implant Material and Method, U.S. Ser. No. 715,098, filed Mar. 22, 1985.

The reconstituted atelopeptide fibrous collagen gel suspension is then cross-linked with a cross-linking agent capable of forming covalent bonds between itself and the collagen. Usually the agent will be polyfunctional, and more usually bifunctional. The cross-linking conditions are such as to produce a covalently cross-linked collagen that may be formulated as an injectable fluid and that provides a desired vaso-occlusive persistence when injected. Aldehydes are preferred cross-linking agents. Examples of aldehydes that may be used to cross-link the collagen are formaldehyde, acetaldehyde, glyoxal pyruvic aldehyde, and dialdehyde starch. Glutaraldehyde is particularly preferred. Compounds that have functional groups that react with the functional groups of the cross-linking agent (e.g., aldehyde group) to form water soluble adducts may be used to quench the cross-linking reaction. Quenching agents that have free amino groups, such as amino acids are preferred.

The concentration of collagen in the suspension at the time of cross-linking, the concentration of cross-linking agent, and the duration of cross-linking reaction are important process conditions as regards obtaining the kind and degree of cross-linking that provides a product having enhanced injectability. To produce predominantly intrafibrillar cross-linking, the collagen must be present at relatively low concentrations. The collagen concentration at the time of cross-linking will usually be in the range of 0.1 to 10 mg/ml, more usually 1 to 5 mg/ml. The concentration of glutaraldehyde in the reaction mixture will typically be about 0.001% to about 0.05% by weight.

The duration of the cross-linking reaction will usually be in the range of one-half hr to about one week. The reaction will normally be carried out at about 10° C. to about 35° C. The quenching agent is added in at least stoichiometric proportions relative to the cross-linking agent. A particularly preferred cross-linking protocol is: about 3 mg/ml collagen concentration; about 0.01% by weight glutaraldehyde for about 16 hr at approximately 22° C. Co-owned U.S. Patent Application for Injectable Cross-linked Collagen Implant Material, Ser. No. 663,478, filed Oct. 22, 1984, details methods for cross-linking collagen fibers.

As noted above, the persistence of the injected material is generally enhanced as the extent of the cross-linking increases. Typically, in producing a collagen meterial having an expected persistence of up to about 2-3 months, the cross-linking reaction is carried out under conditions like those described above, but with a glutaraldehyde concentration of between about 0.1 and 1.0%. The use of collagen material cross-linked with 0.7% glutaraldehyde is described below with reference to FIGS. 2A and 2B. For persistence times greater than about three months, the material should be cross-linked with glutaraldehyde at concentrations up to about 1.0–2.5%.

After the cross-linking reaction has been terminated, the cross-linked atelopeptide collagen product may be washed with an aqueous buffer solution to remove unreacted aldehyde, aldehyde polymers, and, if quenching is employed, unreacted quenching agent and aldehyde-quenching agent adducts. A sodium phosphate-sodium chloride buffer solution, pH 6.9 to 7.4, is preferred.

The collagen material may be mixed, prior to injection, with a contrast agent which allows the injected material to be visualized by X-ray. This can be used to confirm that the occlusive agent has localized in the tumor area of interest. Preferred contrast agents include various iodine-containing organic compounds such as diatrizoate meglumine, diatrizoate sodium, iopidamide meglumine, iothalamate meglumine, iothalamate sodium, metrizoic acid, methiodal sodium, metrizamide, iohexol, iopamidol, and ioxaglate. Tantalum powder and barium sulfate are examples of water-insoluble contrast medium that may be used in the invention. The vaso-occlusive composition will contain a sufficient amount of the contrast material to permit the composition to be visualized under radiographic (X-ray) examination. The composition will usually contain about 30 to about 80 g/100ml of diatrizoate meglumine USP.

The buffers that are used to adjust the pH of the radiopaque vaso-occlusive mixture are those commonly used to buffer aqueous pharmaceutical formulations in the pH range of about 6 to 8. Examples of such buffers are citrate, phosphate, and bicarbonate. After addition of buffered solution of contrast material, the concentration of suspended collagen in the mixture will be in the range of about 0.5 to about 50 mg/ml. For occluding vessels in the 20–150 micron size range, a final collagen concentration of between about 0.5 mg/ml and 3.0 mg/ml is preferred.

3. Vaso-Occlusion

The vaso-occlusive material prepared as above is injected into a major arterial vessel supplying the tumor to produce occlusion of the smaller tumor vessels, i.e., those lumen diameters of between about 10 and 150 microns. The material is preferably injected by a catheter positioned at a selected site of injection in the blood vessel. It will be appreciated that the catheter used in localizing the solid tumor and its main supply vessel, as described above, may also be used for delivering the vaso-occlusive material.

In the usual case the tumor and supply vessel will have the anatomical relationship shown in FIG. 1, where the tumor is supplied peripherally by a major artery which also supplies blood to normal tissue on upstream and downstream sides of the tumor. With this configuration, it is advantageous to block the vessel at the downstream side of the tumor before expelling the material. Otherwise, much of the injected material will be carried downstream in the larger vessel. Conventional types of single-balloon catheters can be used for this purpose.

A preferred type of catheter for use in the present invention is a double-balloon catheter of the type invented by the inventor and Dr. Gabriel Vegh of Advanced Cardiovascular System, Inc. (Palo Alto, CA). This catheter, which is shown at 40 in FIG. 1, has a pair of balloons 42, 44 which are independently inflatable, in situ, by pneumatic supply tubes 46, 48, respectively. The collagen material is supplied to the vessel through a third tube 50 which terminates adjacent the upstream balloon and which encases tubes 46, 48, up to the position of balloon 44. Tube 46 is carried slidably within tubes 50 and affixed to a metal guide wire (not shown), allowing downstream balloon 42 to be moved laterally with respect to the upstream balloon, with the catheter placed in the vessel, to produce a desired spacing between the two balloons.

In operation, catheter 40 is threaded along the vessel of interest, and may be used initially, in a conventional manner, for delivering a radio-opaque agent to the vessel, for purposes of localizing the tumor and/or supply vessel. The catheter is then manipulated to place the upstream and downstream balloons adjacent the upstream and downstream ends of the vessel segment feeding the tumor. This arrangement is illustrated in FIG. 1, showing balloons 42, 44 positioned adjacent the opposite end regions of the tumor. The balloons are then inflated, constricting the vessel adjacent opposite sides of the tumor, and the vaso-occlusive material injected under pressure into the vessel segment. It can be appreciated that the catheter allows the occlusive material to be injected into the tumor under pressure, and in a highly localized manner.

In a second general anatomical configuration, the solid tumor to be treated is supplied by an arterial vessel which feeds into—i.e., terminates within—the tumor. With this configuration, the occlusive material can be injected into the tumor site selectively using a single-balloon catheter to occlude the upstream side of the injection site, or may be injected under low pressure without vessel occlusion. This configuration is usually encountered in malignancies within kidney and liver.

The volume of vaso-occlusive material which is injected into the tumor site will vary according to (a) the concentration of occlusive material, (b) size of the tumor, and (c) the extent to which the injected material can be localized at the tumor site. In a typical vaso-occlusion procedure, for treatment of a solid tumor having a volume between about 5 and 1000 cc, and using a collagen material at a concentration of about 0.5 to 3.0 mg protein/ml, the total volume of material injected is between about 1 and 200 ml. More generally, the injecting step may be carried out by following the infusion of contrast/collagen material into the tumor, by real-time fluoroscopy, and injecting material until a selected-size region becomes occluded. Adequate occlusion is indicated by progressive slowing of normal flow until complete cessation and ultimately, reversal of direction of normal flow is obtained.

According to an important feature of the invention, the vascular occlusion produced by the injected collagen material is confined substantially to the secondary and tertiary vessels in the tumor, including vessels or vessel portions which are distal to collateral vessels which may also supply the tumor tissue. The occlusive material thus acts to restrict blood flow to the tumor from both direct and collateral sources. This effect can be seen in FIG. 1, where injection of material into the occluded vessel segment forces the material primarily into the arterial network supplying the tumor. With occlusion of the secondary and tertiary vessels, such as vessels 30, 34, in the tumor, these vessels are no longer operative in a collateral system involving vessels in the adjacent normal tissue, e.g., from primary vessel 22.

The degree and persistence of vaso-occlusion which is produced, according to the invention, after injection with cross-linked collagen material, in this case cross-linked with 0.007% glutaraldehyde, was examined. The hepatic artery in a mongrel dog was localized by angiography and cross-linked material, at a concentration of about 1 mg/ml, in 60% diatrizoate, meglumine, USP was injected into the vessel supplying the tumor, at a total volume of about 50 ml. Two weeks after injections, the liver was removed, sectioned, and stained for light microscopy. Tissue vessels, having lumen diameters of from 20 to 150 microns, were found to be completely occluded. The effects of hyperthermia on the vaso-occluded tissue will be described below.

The extent of vaso-occlusion in identically treated was examined 2 months after injection. At this stage, light-microscopic examination showed that the endothelial cells lining the vessel lumens had begun to engulf the occlusive material and re-establish an interior lumen. After three months, the lumens were substantially cleared.

4. Heating the Tumor Region

Hyperthermic treatment is performed by heating the vaso-occluded tumor to produce tissue necrosis selectively in the occluded tumor region, either by extended heating alone or in conjunction with radiation or chemotherapy.

A variety of known methods for heating tissue may be used. These include microwave and ultrasonic heating, and where the tumor region lies close to the body surface, dielectric heating or direct contact with a heating pad. Methods for operating and controlling such heating devices, to achieve focused heating in a selected tumor region, are known.

The tumor is preferably heated to a temperature of between about 42° C. to 46° C. The heating temperature will typically be one at which a significant temperature differential between occluded tumor tissue and non-occluded tissue is achieved. As indicated above, an important feature of the invention is the ability to produce differential heating in tumor and adjacent tissue, due to the localized nature of the occlusion and the elimination of collateral circulation. In practicing the invention, the tumor temperature is preferably raised until a desired temperature differential of preferably between about 2° C. and 4° C. is attained. The temperature of tumor and adjacent, non-occluded tissue can be measured in a conventional manner, for example, by placing thermocouples, thermistors or other types of temperature probes at or near the tumor site. The probes may be positioned conveniently by catheter placement in many cases.

The tumor is heated at the above temperature and/or temperature differential for a period calculated to produce selective tumor destruction. The extent of tissue destruction generally increases proportionally with increased heating time above about 42° C., and, as noted above, this time becomes proportionally less as the tissue temperature is raised. The amount of tissue destruction produced under defined temperature and time conditions can be measured directly, such as by determining the metabolic activity or histological features of biopsied material after treatment. Preferably, to avoid surgical invasion, the heating is applied for a period which has been determined from an earlier experimental or clinical study to cause significant tissue damage. The heating period will generally range between a minimum time, at which only minor tissue damage in the adjacent, non-occluded tissue occurs and a maximum time, at which tissue destruction in the occluded tumor begins to plateau. Typically, the tumor is heated for between about 2–8 hr at a tumor temperature of about 42° C., and for proportionately shorter time periods at temperatures above 42° C. It can be appreciated that, with a temperature differential of 2° C. or greater, the heating time can be adjusted to produce at least about four times more tissue necrosis in the occluded tumor tissue than in the adjacent, non-occluded tissue. If necessary, the occluded tumor may be heat-treated in the above manner at selected intervals during the several weeks or months of persistence of the occlusive material.

To illustrate, a group of dogs having spontaneous tumors of the extremities (2 animals), nose (1 animal), and chest wall (1 animal) were treated by the hyperthermia procedure described. In each animal, the tumor and major arterial vessel supplying it were identified by angiography. The tumor regions in each animal were heated by ultrasound for a period of four minutes, with temperature monitoring at multiple locations within the tumor and the surrounding tissue. The tumor region was then selectively occluded by injecting cross-linked collagen into the tumor's major supply artery, and heated a second time under identical conditions. Comparison of pre- and post-occlusion heating showed that (a) heating was more rapid in vaso-occluded material, comparing both tumor tissue before and after occlusion and tumor and surrounding tissue after occlusion; (b) differential heating between tumor and surrounding tissue was enhanced substantially after vaso-occlusion; and (c) the temperature drop in vaso-occluded tissue after heating was slower than in non-occluded tissue.

One of the animals was treated by heating the occluded tumor at 46° C. for 30 minutes. Follow-up showed no tumor regrowth.

The selective temperature effects described above may also be used to enhance tumor damage by radiation or chemotherapeutic agents, according to another general method of practicing the invention. The treatment method is readily combined with radiation therapy by irradiating the tumor in a conventional manner and following completion of radiation therapy, occluding the tumor and heating the occluded tumor region to a selected temperature, as described earlier. When the invention is used as an adjunct to chemotherapy, consideration must be given to the problem of delivering the drug to vaso-occluded tissue. This problem may require that the drug be administered to the tissue before injecting the occluding material, or be included with occlusive material. The latter approach has the advantage that the drug/collagen material can be formulated to provide controlled release of the drug from the collagen matrix which forms in the vessels.

From the foregoing, it can be appreciated how various objects and features of the invention are met. The vaso-occlusive collagen material used in the invention is easily administered by catheter, and the material can be injected into the tumor region in a highly localized manner by occluding the vessel on one or both sides of the segment of vessel which supplies the tumor. The vaso-occlusive material may contain a contrast agent that allows the infusion of injected material into the tumor to be visualized fluoroscopically.

The vaso-occlussive effect is specific for vessels whose lumen diameters are substantially in the 10-150 micron size range, producing occlusion of secondary and tertiary vessels, distal to collateral vessels which may supply the tumor from primary vessels outside of the zone of occlusion. The nearly complete "internal" occlusion and lack of collateral supply significantly reduces the heat capacitance of the tumor—i.e., the capacity to absorb energy in relation to the change in temperature. The reduced heat capacitance is reflected by a more rapid temperature rise on heating, and by a temperature differential, with respect to surrounding tissue, of up to 2°-9° C. The heat response of the tumor can be exploited for selective tumor destruction.

The ability of cross-linked collagen to persist for up to several months in situ allows repeated hyperthermia treatments over a several-week or -month period, without having to introduce the additional occlusive material. Alternatively, additional occlusion of newly formed vessels may be carried out by subsequent infusion of collagen through primary vessels. Persistent collagen occlusion, by limiting blood flow to the tumor over an extended period, may also contribute to selective tumor destruction through hypoxic effects.

While preferred embodiments of the invention have been described herein, it will be apparent that various changes and modifications may be made without departing from the invention.

It is claimed:

1. A method of treating a solid tumor comprising:
   a. localizing the tumor and the arterial vessel that supplies it,
   b. providing a collagen vaso-occlusive material adapted to produce occlusion of blood vessels having lumen diameters between about 10 and 150 microns,
   c. injecting said material into said arterial vessel,
   d. by said injecting, producing vaso-occlusion of the secondary and tertiary vessels supplying the tumor, distal to the collateral blood vessels which may also supply the tumor, and
   e. heating the tumor under conditions which produce tissue necrosis selectively in the occluded tumor tissue.

2. The method of claim 1, wherein said heating is effective to raise the temperature of the occluded tumor tissue to at least about 42° C.

3. The method of claim 1, wherein said heating is effective in raising the temperature of the occluded tumor tissue to between about 44° and 46° C.

4. The method of claim 1, wherein said heating is effective to produce a temperature differential between the occluded tumor tissue and the adjacent, non-occluded tissue of at least about 2° C.

5. The method of claim 4, wherein said heating is applied for a period calculated to produce at least about four times more tissue necrosis in the occluded tumor tissue than in adjacent, non-occluded tissue.

6. The method of claim 5, wherein said heating is effective to raise the tumor temperature to at least about 44° C., and said heating is applied for a period of at least about 30 minutes.

7. The method of claim 1, wherein the collagen material includes a suspension of chemically cross-linked atelopeptide collagen which is adapted to persist in such secondary and tertiary vessels, after said injecting, for a period of at least about two weeks.

8. The method of claim 7, which further includes repeating said heating step during the period of vaso-occlusive persistence.

9. The method of claim 7, wherein the collagen material is cross-linked under conditions which produce predominantly intrafibrillar cross-links, and the period of vaso-occlusive persistence is less than about two months.

10. The method of claim 9, wherein the collagen material is cross-linked by reacting enzyme-solubilized collagen atelopeptide with about 0.005%–0.1% glutaraldehyde.

11. The method of claim 7, wherein the collagen material is cross-linked under conditions which produce interfibrillar cross-links, and vaso-occlusion persists for up to two months.

12. The method of claim 11, wherein the collagen material is cross-linked by reacting enzyme-solubilized collagen atelopeptide with about 0.1%–2.5% glutaraldehyde.

13. The method of claim 7, wherein the collagen material includes a radio-opaque agent which permits the area of vaso-occlusion to be visualized by fluoroscopy.

14. The method of claim 1, wherein the tumor receives its blood supply from along a segment of such vessel, and said injecting includes blocking the distal end of such segment and delivering the collagen material to the vessel just proximal to such blocked distal end.

15. The method of claim 14, which further includes blocking the proximal end of such segment prior to said delivering.

* * * * *